United States Patent
Moore

(10) Patent No.: US 6,890,878 B2
(45) Date of Patent: May 10, 2005

(54) CATALYST FORMULATION COMPRISING CERAMIC FOAM MATERIAL

(75) Inventor: John H. Moore, Warren, PA (US)

(73) Assignee: United Refining Company, Warren, PA (US)

( * ) Notice: Subject to any disclaimer, the term of this patent is extended or adjusted under 35 U.S.C. 154(b) by 326 days.

(21) Appl. No.: 10/028,322

(22) Filed: Dec. 28, 2001

(65) Prior Publication Data

US 2003/0125594 A1 Jul. 3, 2003

(51) Int. Cl.$^7$ .................. B01J 21/04; B01J 27/224; C04B 35/00; B32B 3/00; B32B 5/22
(52) U.S. Cl. ................ 502/439; 502/178; 502/208; 502/214; 502/232; 502/412; 502/527.14; 502/527.16; 502/527.24; 501/1; 501/80; 501/88; 501/154; 428/312.2; 428/312.6; 428/313.3; 428/317.9
(58) Field of Search .................. 502/178, 208, 502/232, 214, 412, 439, 527.14, 527.16, 527.24; 501/1, 80, 88, 154; 428/312.2, 312.6, 313.3, 317.9; 429/317.9

(56) References Cited

U.S. PATENT DOCUMENTS

| | | | | |
|---|---|---|---|---|
| 3,686,334 A | * | 8/1972 | Britton | ................ 568/896 |
| 3,947,504 A | * | 3/1976 | Kyo et al. | ................ 568/923 |
| 4,647,499 A | * | 3/1987 | Takahashi et al. | ....... 428/312.6 |
| 4,810,685 A | | 3/1989 | Twigg et al. | |
| 4,853,351 A | * | 8/1989 | Takahashi et al. | ............ 501/87 |
| 5,510,056 A | | 4/1996 | Jacobs et al. | |
| 5,658,497 A | | 8/1997 | Kumar et al. | |
| 6,258,600 B1 | | 7/2001 | Zhang et al. | |
| 6,291,603 B1 | | 9/2001 | Glover | |

* cited by examiner

Primary Examiner—Mark L. Bell
Assistant Examiner—Patricia L. Hailey
(74) Attorney, Agent, or Firm—Burns, Doane, Swecker & Mathis, L.L.P.

(57) ABSTRACT

Provided is a catalyst formulation which exhibits extended catalyst life. The formulation comprises a mixture of a ceramic foam material uniformly interspersed between the solid catalyst particles, with the volume percent of ceramic material in the mixture preferably ranging from 20 to 60 volume %. The catalyst formulation is particularly applicable to solid catalyst particles comprised of a phosphoric acid impregnated substrate, and is particularly useful for processes such as catalytic hydrocarbon condensation processes.

14 Claims, No Drawings

CATALYST FORMULATION COMPRISING CERAMIC FOAM MATERIAL

BACKGROUND OF THE INVENTION

1. Field of the Invention

The present invention relates to a novel catalyst formulation. In particular, the formulation comprises a mixture of ceramic foam material and solid catalyst particles. The ceramic foam material is uniformly dispersed with the solid catalyst particles. The present invention also relates to a method of improving the catalyst life of a solid polymerization catalyst by uniformly blending reticulated ceramic foam material with the solid catalyst particles.

2. Description of Related Art

Typically, chemical reactor beds include discrete solid catalyst particles contained in one or more fixed beds. Many different techniques are available to increase the efficiency of the catalyst beds and to improve the catalyst life. One such method involves providing filtration of solids from organic based feedstreams to the chemical reactors, and providing flow distribution to the chemical reactors, by employing a reticulated ceramic material as a filter for the organic based feedstream prior to contact with the catalyst particles. See for example U.S. Pat. Nos. 6,258,600 and 6,291,603. The foregoing patents also note that the reticulated ceramic foam material can be coated to act as a catalyst in order to react with some of the impurities. The use of ceramic foams as a catalyst, generally as a base impregnated with an active material, is well known. See for example U.S. Pat. Nos. 5,510,056; 5,658,497 and 4,810,685.

The physical integrity of the catalyst particles also has a significant impact on the catalyst run length of a process. How quickly a catalyst breaks down and reduces void area determines when a process must be shut down in order to replace the catalyst.

Hydrocarbon polymerization units, such as motor fuel condensate units, are typically shut down every six to seven weeks due to high pressure drop across the reactor catalyst beds. Such catalysts, which can be made of, for example, diatomaceous earth impregnated with phosphoric acid, gradually break down and become structurally unstable as the run progresses. The rate of change of this instability can be controlled partially by operating conditions, such as, water content, injection rates into the feed, temperature and pressure. Regardless of how well the unit is operated, however, the final result is mechanical decay of the structural integrity of the catalyst. As the catalyst breaks down, the catalyst migrates into the openings that normally exist between the catalyst particles, thereby resulting in a loss of void area. This void area is critical in providing a space for the hydrocarbon feed that must flow across the catalyst in order for the reaction to proceed.

The shutdown of the unit and a change out of the catalyst due to the breakdown of the catalyst adds greatly to the economics of a reaction. Avoiding the expense associated with the need for frequent shutdowns and catalyst change would certainly be of great value to the industry. Improving the run length and the unit conversion by somehow avoiding the premature mechanical decay of the structural integrity of the catalyst would certainly result in a more economical and efficient chemical process.

Accordingly, it is an object of the present invention to provide a catalyst formulation which exhibits improved catalyst life and provides improved run length.

Another object of the present invention is to provide a chemical reactor containing the novel catalyst formulation of the present invention, for which unit conversion can be expected to increase as the chemical run progresses.

Still another object of the present invention is to provide a chemical process/unit for which the need for frequent shutdown and catalyst change is avoided.

These and other objects of the present invention will become apparent to the skilled artisan upon a reading of the following specification, and the claims appended thereto.

SUMMARY OF THE INVENTION

In accordance with the foregoing objectives, the present invention provides one with a catalyst formulation exhibiting extended catalyst life. The formulation comprises a mixture of a ceramic foam material uniformly interspersed between solid catalyst particles. The ceramic foam material may be any commercially available material, for example, a product having a composition comprising silicon carbide which is available from SELEE Corporation, of Hendersonville, N.C. It is most preferred that the volume percent of ceramic foam material in the catalyst formulation mixture be in the range of from 20 to 60%.

In another embodiment of the present invention, there is provided a process of polymerizing hydrocarbons which comprises passing a hydrocarbon feedstream through a catalyst bed comprised of the catalyst formulation of the present invention. The catalyst formulation of the present invention finds particular applicability in processes for polymerizing hydrocarbons, such as the oligomerization of light olefins to produce liquid olefinic products, or the alkylation of aromatics with gaseous olefins to yield high purity alkyl aromatics. In a preferred embodiment, the solid catalyst particles employed are comprised of diatomaceous earth impregnated with phosphoric acid. The use of such catalysts are applicable to catalytic condensation processes, which are useful in motor fuel production.

Among other factors, the present invention is based on the discovery that uniformly blending a ceramic foam material with solid particulate catalysts inserts void area into the catalyst formulation which persists after any detrimental collapse of the catalyst. Thus, even when the catalyst collapses, the void area of the catalyst bed will remain substantial because of the presence of the ceramic foam material. Moreover, as the catalyst begins to breakdown, i.e., break apart, the surface area in the reactor catalyst bed will be improved by the particles migrating into the pores of the ceramic foam material. The result is increased conversion and catalyst run life, with a direct economic benefit for not having to shutdown and change the catalyst as frequently.

DETAILED DESCRIPTION OF THE PREFERRED EMBODIMENTS

The catalyst formulation of the present invention comprises a mixture of a ceramic foam material uniformly interspersed between solid catalyst particles. The solid catalyst particles can be any particulate catalyst available and used in chemical reactions. The present invention is directed to preventing the total loss of void area in the catalyst bed upon collapse of the catalyst particles, and therefore application of the present invention is particularly directed to those solid catalyst particles for which mechanical decay of the structural integrity of the catalyst is a problem. Advantages are particularly realized when the solid catalyst particles are phosphoric acid impregnated catalysts. Such catalysts are well known for hydrocarbon condensation processes and are available from UOP of Des Plaines, Ill. under the designation SPA (solid phosphoric acid). Two such solid phosphoric acid catalysts commercially are available under the designations SPA-1 and SPA-2.

An important aspect of the present invention is the uniform blending of a ceramic foam material in with the solid catalyst particles to uniformly intersperse the ceramic foam material between the solid catalyst particles. By uniformly interspersing the ceramic foam material between the solid catalyst particles, one effectively inserts void area within the catalyst formulation which will persist after any loss that results from the collapse of the catalyst. Flow of the feed stream may be more restricted, but not to the point that a shutdown is required. It is the collapse of the catalyst which closes off the flow path through the catalyst bed, thus ending the useful life of the catalyst. It has been found that the presence of the ceramic foam material maintains the void area after the collapse of the catalyst and thus extends the useful life of the catalyst, and hence the reaction run length.

It has also been discovered that as the catalyst particles do breakdown, effective catalyst surface area will be regained by the particles migrating into the foam pores. As the ceramic foam is loaded up with catalyst fines or fragments, the catalyst surface area available for reaction is increased, and thus the unit conversion increases as the run progresses. The result is that the unit run length can be significantly increased by the ceramic foam material maintaining void area as the collapse of the catalyst begins, and the unit conversion can be expected to increase as the run progresses when the catalyst does breakdown due to the migration of the catalyst fines into the pores of the ceramic foam material. A tremendous cost saving is thereby realized as the need to shutdown and change catalyst is greatly reduced.

In a preferred embodiment of the present invention, the volume percent of ceramic foam material interspersed between the solid catalyst particles in the mixture ranges from 20 to 60%, more preferably from 40 to 60%, and most preferably from 45 to 55 volume %. The foregoing percentage ranges are preferred because too much foam will adversely impact the unit conversion, especially at the beginning of the run, while too little foam will not provide the necessary void area needed to prevent the pressure drop from building. Therefore, utilization of the ceramic foam material in the mixture in the aforenoted ranges is most preferred.

The ceramic foam material blended with the solid catalyst particles can be any conventional material such as that commercially available from SELEE Corporation, in Hendersonville, N.C. One example of a commercially available material is a product with the composition comprised of silicon carbide. Other known and available foam ceramic materials may also be used.

The shape of the reticulated ceramic foam material can be any suitable shape, for example, the material can be in the shape of cubes. However, it is important that the material have a suitable porosity as this allows migration of the solid catalyst particles during breakdown into the pores of the ceramic foam support material. It is preferred that the porosity of the ceramic material be in the range of from 10 to 800 pores per linear inch ("ppi"), more preferably in the range of from 10 to 80 ppi, and most preferably in the range of from 10 to 30 ppi.

The ceramic foam material itself must also have an appropriate void space or void area in order to realize the advantages of the present invention. The amount of void area must balance the crush strength of the material and the void volume. Too much void space and the crush strength of the ceramic foam particles will be too small for the ceramic foam to be effective, yet the more void volume the better in terms of maintaining void space once the catalyst particles begin to collapse. A void space of the ceramic foam in the range of from about 80% to about 85 volume % has been found to be preferred, with a void space of about 85 volume % being most preferred.

With such a void space, the crush strength of the ceramic foam material is preferably in the range of from about 100–600 lbs/sq. inch, more preferably in the range of from 300–550 lbs/sq. inch, and most preferably in the range of from about 400–500 lbs/sq. inch.

The size of the ceramic foam particles, e.g, cube shaped particles, is most preferably the size of the catalyst particles, for this would allow for the most uniform of dispersions. However, practical considerations often can require the ceramic foam particles to be larger than the catalyst particles. The size of the ceramic foam particles, however, can be chosen adequately based upon the practical considerations, with the characteristics of ppi, void area and crush strength being more importantly observed as discussed above.

In preparing the catalyst composition of the present invention, one simply blends the ceramic foam material with the solid catalyst particles in the desired, appropriate percentage. The mixing is simple physical mixing, and can be accomplished, for example, in a drum mixer. The mixing continues until the mixture is uniform, with the ceramic foam particles being as uniformly interspersed between the catalyst particles as possible.

The mixture is then inserted into the catalyst bed in a chemical reactor. The insertion can be by any conventional means.

As well, the composition of the present invention can be used in any conventional chemical reactor which employs a catalyst bed, e.g., a chamber type reactor or a tubular type reactor. The reactors can also contain one or more catalyst beds, can involve upflow of feedstream or downflow of feedstream. The processes run in the reactor will, of course, depend on the catalyst particles employed, as well as the feedstream fed to the reactor. Generally, any type of reaction can be run in accordance with the present invention whereby solid catalyst particles are employed. Particular application has been found, however, with regard to the reaction of hydrocarbons, and preferably the polymerization of hydrocarbons. In practicing the process of the present invention, a hydrocarbon feedstream is simply passed through a catalyst bed comprised of a mixture of ceramic foam material uniformly interspersed between solid catalyst particles.

A preferred reaction to which the present invention is applicable is the oligomerization of light olefins to produce liquid olefinic products, such as polygasoline, nonene, and dodecene. The alkylation of aromatics with gaseous olefins to yield high purity alkyl aromatics, such as cumene, is also a preferred reaction. Both of these types of reactions can be conducted in a condensation unit using solid phosphoric acid catalysts. Such catalysts, as described above, are generally phosphoric acid impregnated catalysts, with the catalyst substrate preferably being diatomaceous earth, or some other inorganic substrate.

In a preferred embodiment, the original ceramic foam particles, before the start up of a process, are seeded with spent catalyst fines. Such seeding will increase the conversion of the process during its initial stage. This seeding can be accomplished by simply pouring the catalyst fines over the ceramic foam, and then mixing the seeded ceramic foam with the solid catalyst particles. Alternatively, the mixture of ceramic foam material and solid catalyst particles can be seeded by simply pouring the catalyst fines over the mixture, either before or after the mixture has been inserted into the reactor.

Another advantage, both economic and practical, of the present invention is the re-use of the ceramic foam. The used ceramic foam material, once separated from spent catalyst, can simply be mixed with fresh catalyst. The used ceramic foam material will also contain catalyst fines, so seeding to improve initial conversion is unnecessary.

The present invention, therefore, improves the life of a solid particulate catalyst by uniformly interspersing between the solid catalyst particles a ceramic foam material. It is preferred that the amount of the ceramic foam material used in the mixture is in the range of from about 20 or 30 to about 60 volume %. The resulting economic advantages of the present invention are quite large, as the insertion of the ceramic foam material allows for void space to persist even upon the mechanical decay of the structural integrity of the catalyst, thereby significantly increasing run length. Also, the presence of the ceramic foam material increases unit conversion as the run progresses by providing pores into which the catalyst can migrate as it begins to breakdown. The migration of the catalyst into the holes of the ceramic material actually increase the catalyst surface available for reaction. As a result, the operation of the chemical reactor using the catalyst composition of the present invention can be more effective, and it need not be shutdown as often, and the catalyst need not be changed as often.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A catalyst composition which comprises a ceramic foam material interspersed between solid catalyst particles.

2. The catalyst composition of claim 1, wherein the ceramic foam material is comprised of a silicon carbide composition.

3. The catalyst composition of claim 1, wherein the ceramic foam material is in the shape of hollow cubes.

4. The catalyst composition of claim 1, wherein the porosity of the ceramic foam material is in the range of from 10 to 800 pores per linear inch.

5. The catalyst composition of claim 4, wherein the porosity is within the range of 10 to 80 pores per linear inch.

6. The catalyst composition of claim 4, wherein the porosity is in the range of 10 to 30 pores per linear inch.

7. The catalyst composition of claim 1, wherein the void space in the ceramic foam material ranges from about 80 to about 85 volume %.

8. The catalyst composition of claim 7, wherein the void space is about 85 volume %.

9. The catalyst composition of claim 1, wherein the crush strength of the ceramic foam material ranges from 100 to 600 lbs/sq. inch.

10. The catalyst composition of claim 9, wherein the crush strength of the ceramic foam material ranges from 400 to 500 lbs/sq. inch.

11. The catalyst composition of claim 1, wherein the percentage of ceramic foam material in the mixture, based on volume, ranges from 20 to 60%.

12. The catalyst composition of claim 1, wherein the solid catalyst particles comprise diatomaceous earth.

13. The catalyst composition of claim 1, wherein the solid catalyst particles comprise a solid phosphoric acid catalyst.

14. The catalyst composition of claim 13, wherein the solid catalyst particles comprise a diatomaceous earth impregnated with phosphoric acid.

* * * * *